US011135159B2

(12) United States Patent
Wilhelm et al.

(10) Patent No.: US 11,135,159 B2
(45) Date of Patent: Oct. 5, 2021

(54) OPTIMIZED HIGH-DOSE MESALAZINE-CONTAINING TABLET

(71) Applicant: Dr. Falk Pharma GmbH, Freiburg (DE)

(72) Inventors: Rudolph Wilhelm, Bischweier (DE); Markus Pröls, Freiburg/Breisgau (DE); Roland Greinwald, Kenzingen (DE); Tanju Nacak, Gottenheim (DE)

(73) Assignee: Dr. Falk Pharma GmbH

( * ) Notice: Subject to any disclaimer, the term of this patent is extended or adjusted under 35 U.S.C. 154(b) by 0 days.

(21) Appl. No.: 15/770,569

(22) PCT Filed: Oct. 21, 2016

(86) PCT No.: PCT/EP2016/075427
§ 371 (c)(1),
(2) Date: Apr. 24, 2018

(87) PCT Pub. No.: WO2017/072050
PCT Pub. Date: May 4, 2017

(65) Prior Publication Data
US 2018/0311155 A1 Nov. 1, 2018

(30) Foreign Application Priority Data

Oct. 30, 2015 (EP) .................................. 15192269

(51) Int. Cl.
| *A61K 9/20* | (2006.01) |
| *A61K 9/28* | (2006.01) |
| *A61P 1/00* | (2006.01) |
| *A61K 9/00* | (2006.01) |
| *A61K 31/606* | (2006.01) |

(52) U.S. Cl.
CPC .......... *A61K 9/0065* (2013.01); *A61K 9/2027* (2013.01); *A61K 9/2072* (2013.01); *A61K 9/2846* (2013.01); *A61K 9/2866* (2013.01); *A61K 31/606* (2013.01); *A61P 1/00* (2018.01)

(58) Field of Classification Search
None
See application file for complete search history.

(56) References Cited

U.S. PATENT DOCUMENTS

| 4,540,685 A | | 9/1985 | Bauer | |
| 5,686,105 A | * | 11/1997 | Kelm | A61P 29/00 424/452 |
| 6,277,412 B1 | | 8/2001 | Otterbeck | |
| 6,962,717 B1 | | 11/2005 | Huber et al. | |
| 2003/0114527 A1 | * | 6/2003 | Karnachi | A61K 31/196 514/567 |
| 2006/0127484 A1 | * | 6/2006 | Speirs | A61K 9/5084 424/489 |
| 2009/0162434 A1 | * | 6/2009 | Ugwoke | A61K 9/2846 424/472 |
| 2009/0298797 A1 | * | 12/2009 | Zheng | A61K 31/155 514/161 |
| 2009/0317459 A1 | * | 12/2009 | Pennel | A61K 9/1611 424/451 |
| 2013/0183434 A1 | * | 7/2013 | Fluiter | A61K 9/2846 427/2.21 |
| 2015/0196518 A1 | | 7/2015 | Khera et al. | |
| 2015/0374632 A1 | * | 12/2015 | Ryu | A61K 9/2846 424/480 |

FOREIGN PATENT DOCUMENTS

| EP | 0083775 A2 | 12/1982 | |
| EP | 0977557 B1 | 4/1998 | |
| EP | 1198226 B1 | 6/2003 | |
| EP | 2425826 A1 | 3/2012 | |
| EP | 2621477 B1 | 3/2014 | |
| GA | 2444814 A1 | 5/2002 | |
| WO | WO 00/44353 A1 | 8/2000 | |
| WO | WO-03045356 A1 * | 6/2003 | ........... A61K 9/2846 |
| WO | 2004093884 A2 | 11/2004 | |
| WO | WO 2009/047802 A2 | 4/2009 | |
| WO | WO 2011/045775 A1 | 4/2011 | |
| WO | 2012089677 A1 | 7/2012 | |
| WO | WO 2015/062640 A1 | 5/2015 | |

OTHER PUBLICATIONS

International Search Report in PCT/EP2016/075427, dated Dec. 6, 2016.
International Written Opinion in PCT/EP2016/075427, dated Dec. 6, 2016.
International Preliminary Report on Patentability in PCT/EP2016/075427, dated Jan. 16, 2018.

* cited by examiner

*Primary Examiner* — David J Blanchard
*Assistant Examiner* — John P Nguyen
(74) *Attorney, Agent, or Firm* — Curatolo Sidoti Co., LPA; Salvatore A. Sidoti; Brittany L. Kulwicki

(57) ABSTRACT

The present invention relates to an oral enteric high-dose tablet comprising mesalazine as the active substance as well as its use.

14 Claims, 2 Drawing Sheets

Figure 1:
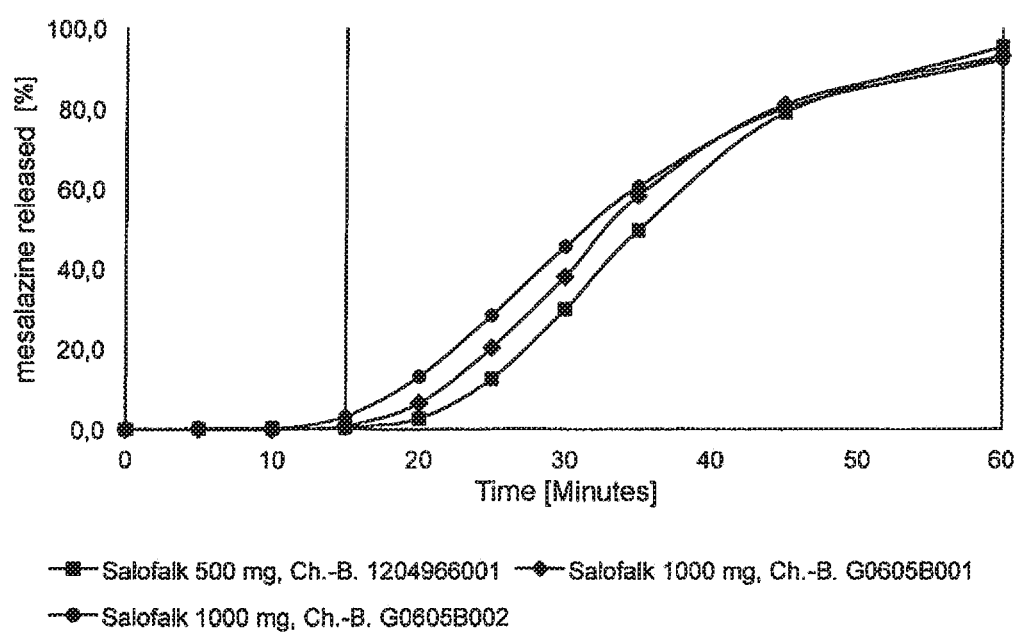

Error bars indicate scattering of the results (minimum and maximum measured value each).

OPTIMIZED HIGH-DOSE MESALAZINE-CONTAINING TABLET

CROSS REFERENCE TO RELATED APPLICATIONS

This application is a national stage application under 35 U.S.C. § 371 of International Application No. PCT/EP2016/075427, filed 21 Oct. 2016, which claims priority from European Patent Application No. 15192269.7, filed 30 Oct. 2015, which applications are hereby incorporated herein by reference in their entireties.

Chronic inflammatory bowel diseases are intermittent destructing inflammations of the intestinal tract. These comprise the two most frequent types Crohn's disease and ulcerative colitis as well as the more rare collagenous colitis, lymphocytic colitis, and atypical microscopic colitis. Crohn's disease and ulcerative colitis differ in their distribution pattern as well as their macroscopic and histological pictures [Dignass et al, (2012) Journal of Crohn's and Colitis 6, 965-990].

Crohn's disease can segmentally occur in all sections from the esophagus to the rectum and attacks all wall layers. Typical symptoms are algospasm, diarrhea, pyrexia, and loss of weight. Ulcerative colitis begins in the rectum, from here can expand to all sections of the large bowel and circularly only attacks the mucosa. Patients suffer from bloody diarrhea, algospasm, anorexia, and loss of weight. Etiology of the chronic inflammatory bowel diseases is still unclear, so that there is a lack of causal treatment options.

For the therapy and prevention of recurrency of chronic inflammatory bowel diseases such as ulcerative colitis and Crohn's disease mesalazine-releasing medicaments are employed. Mesalazine is the international non-proprietary name for 5-amino salicylic acid. Although the exact mechanism of action is not yet clear, the therapeutic efficacy of the substance can be attributed to a local anti-inflammatory effect on the intestinal wall. Mesalazine is used orally and/or rectally as the first-line treatment. For the oral treatment of the acute episode of ulcerative colitis as well for prevention of recurrency a high-dose therapy with mesalazine has proved to be effective, wherein a daily dose of 3 g is administered once a day or divided into 3 single doses (in the morning, noon, evening).

To prevent absorption of active ingredient in the upper sections of the small intestine after oral application as well as to selectively transport mesalazine to the desired site of action in the intestine particular galenic formulations have to be provided. To achieve this object the single dose of the active ingredient can be formulated either in the form of a monolithic compact dosage form, such as for example an enteric-coated tablet or a tablet with modified release of active ingredients, or as a multi-particulate separated dosage form, such as for example enteric-coated granules/pellets or granules/pellets with modified release of active ingredients. These forms of administration are known, avoid a premature release of active ingredients, and instead permit retarded, continuous, or discontinuous release of the drug dose as well as taking mesalazine to the desired target site. Here, the monolithic dosage form has the advantage that generally the volume is smaller with the same dose and composition than that of a multi-particulate dosage form. Thus, tablets for many patients are easier to swallow than the corresponding multi-particulate forms with the same dose.

In addition to such galenic requirements the correct taking of the medicament as well as the exact adherence to the dosage instructions and type and duration of use by the patients are an essential requirement for the efficacy of a mesalazine treatment. Compliance shows itself in how exactly and for how long the patient complies with the prescribed dosage scheme. Non-compliance by the patient influences the therapy result up to ineffectiveness.

The World Health Organization (WHO) in addition to social/economic, system-related and disease-related factors describes therapy and patient-related phenomena as reasons for non-compliance. As expressions of therapy and patient-related factors complexity of the treatment regime and duration of the treatment as well as motivation, expectations, and forgetfulness of the patients can be mentioned, among others. Thus, an essential measure to improve compliance is to simplify the therapy with drugs.

Unsuitable dosage schemes for the oral high-dose therapy of inflammatory bowel diseases with mesalazine can impair the everyday life and thus the quality of life of the affected patients. This particularly applies to patients in whom after a successful therapy reoccurrence of the disease is to be prevented. Compliance can significantly be enhanced by administering forms of administration that are comfortable for the patients, by reducing the number of medicaments to be taken, as well as by a simplified dosage scheme. In this context, the daily and correct taking of high daily doses of mesalazine represents a major challenge for the patient.

Various solutions for the use of oral mesalazine preparations are described in the prior art. The therapeutic use of enteric-coated tablets of mesalazine with relatively low amounts of active ingredient such as for example Salofalk® 250 mg/–500 mg enteric tablets (EP 0 083 775), Claversal® 250 mg/–500 mg enteric tablets, or Asacol® 400 mg enteric tablets are established. These forms of administration have film coatings based on polymeric substances with pH-related solubility properties. Depending on the resolution pH value as well as the amount of applied film-forming agent a specific section of the intestine can be selected for the start of the mesalazine release. After the film coating has completely been dissolved in the small intestine a rapid release of mesalazine from the remaining and subsequently disintegrating tablet core can be assumed. Thus, drug release is retarded, but not modified.

Modern mesalazine-containing oral forms of administration also describe high-dose formulations that however have the disadvantage of a very complex pharmaceutical technology. So, there are described multi-particulate formulations in the form of pellets (EP 0 977 557). In EP 0 977 557 there is described an oral pellet formulation having a controlled releasing profile. Here, controlled release is achieved by a complex polymer matrix, in which the active ingredient is present in the core of the pellet, and enteric film coatings. Use of sachets enables the administration of more than 1000 mg mesalazine pellets per sachet. WO 2004/093884 describes the administration of a retarded release mesalazine formulation as a sachet at a dosage between 500 mg to 10 g per sachet. Also, only complex pharmaceutical technologies are known in the form of tablets. In EP 1 198 226 there is also described an inner matrix in which the active substance is at least partially enclosed. Additionally, said oral form of administration contains an outer hydrophilic matrix and optionally further other carriers.

A further high-dose formulation contains a matrix core of a defined viscosity, wherein said hydrophilic matrix has to be present in an amount of 1 to 20% based on the total weight of the tablet (EP 2 621 477).

In WO 2011/045775 there are disclosed tablets having relatively high content of mesalamine (1200 mg per tablet). In the preparation granulated mesalamine is mixed with matrix-forming substances such as Carbopol and subsequently compressed. Said tablets are provided with a single layer of enteric coating agent.

WO 00/44353 describes pharmaceutical compositions for slow release of various active ingredients in the gastrointestinal tract. Here, a number of active ingredient-containing particles are coated with a material that is insoluble in gastric and intestine juice, wherein the individual particles after having been coated with coating agents such as Eudragit® RS or Eudragit® NE are compressed together. Here, the active ingredient-containing core represents a homogenous mixture comprising the active ingredient and a polymer that is insoluble in gastric and intestine juice.

WO 2015/062640 discloses an insulating layer for the accelerated release of active ingredients in the intestine for retarded release pharmaceutical formulations. The tablets described there contain a core with the pharmaceutical active ingredient, an insulation layer that causes an accelerated release of the active ingredient in the intestine and covers the core as well as an outer coating which in turn consists of an inner and an outer layer. The outer and inner layers of the outer coating include polymeric materials that dissolve at a pH value above 6.

WO 2009/047802 describes pharmaceutical formulations for various active ingredients, i.a. 5-amino salicylic acid or its metabolites. These are administered in a bio-adhesive formulation. Retarded release is caused by mixing the active ingredient with a polymer that is insoluble in gastric juice and subsequently compressing. Said matrix tablet is subsequently coated with an enteric coating.

It is the object of the present invention to provide a stable high-dose tablet of mesalazine that enables the administration of 700 mg to 1200 mg of an active ingredient per unit by an optimized recipe. Due to the chosen design and size the tablet can be swallowed without any problems, so that the same therapeutic efficacy such as e.g., with taking twice the number of Salofalk® 500 mg enteric tablets can be achieved with a simplified dosage scheme. This considerably simplifies the therapy with drugs and regular medication intake is ensured. Thus, all the properties of the present invention increase acceptance of the form of administration in the patients and result in an enhanced compliance.

A further aspect of the present invention is that the high-dose tablet of mesalazine is well accepted by the patients. Here it is essential that the tablet, which is relatively large itself, can be swallowed well and without any problems. On the other hand, the high-dose tablet according to the invention should have a release profile of the active ingredient that corresponds to the release profile of two smaller tablets. That is, for example a high-dose tablet of mesalazine with 1000 mg of active ingredient should have a release profile corresponding to the active ingredient profile of two tablets of 500 mg active ingredient each. Moreover, to reduce burden on the patients, the relative proportion of excipients and coating materials should be kept as low as possible. Excipients and coating materials could be tolerated poorly at least by some patients and thus, the proportion should be kept as low as possible.

Thus, the present invention relates to an oral enteric high-dose tablet comprising 700 mg to 1200 mg of mesalazine as the active substance or a pharmaceutically acceptable salt thereof and at least one excipient, wherein the mass of the high-dose tablet is at most 40%, preferably at most 35% and particularly preferred at most 25% higher than the mass of the active substance and wherein the at least one excipient does not contain any matrix-forming substances in the core. The formulation according to the invention is not a matrix tablet in which the release of the active ingredient is controlled by the matrix in the tablet core.

Here, enteric means that the high-dose tablet meets the demands on enteric tablets in accordance with the specifications of the monographs on forms of administration of the European Pharmacopoeia.

As used herein, high-dose tablet means a tablet of a high dose of an active substance. In the present invention, a high dose particularly means an amount of 700 mg to 1200 mg, preferably between 900 and 1100 mg and especially preferred about 1000 mg of the active substance. About 1000 mg means a range of 980 mg to 1020 mg of the active substance, namely mesalazine.

The high-dose tablet according to the invention contains 700 mg to 1200 mg of mesalazine. In one embodiment the high-dose tablet according to the invention contains mesalazine in an amount between 900 and 1100 mg of mesalazine per high-dose tablet and most preferably between 950 mg and 1050 mg of mesalazine per high-dose tablet. In a preferred embodiment the high-dose tablet contains about 1000 mg. In this way, a daily dose of 3 g of mesalazine can be realized either by the single administration of three high-dose tablets or by using three times one tablet each (in the morning, noon, evening).

The at least one excipient is chosen from the common pharmaceutically acceptable excipients for granulation and tablet preparation. Said at least one excipient together with the active ingredient forms the tablet core. Especially preferred the at least one excipient exclusively consists of polyvinyl pyrrolidone, particularly preferably povidone K25.

So, for example the active substance mesalazine is converted to an active ingredient granule by means of a binder solution consisting of water and povidone K25 by wet granulation. Preferably, here povidone K25 is contained in the high-dose tablet in an amount of 50 mg to 80 mg, particularly preferred 66.5 mg to 73.5 mg per 1000 mg of mesalazine.

In a further embodiment the high-dose tablet according to the invention in addition to the excipient that is preferably povidone K25 can contain further excipients selected from dry binders, decomposition aids, flow control agents, and lubricants. Such further excipients are preferably added in an amount of at most 180 mg per 1000 mg of mesalazine.

For example, dry binders are selected from the group comprising calcium phosphates, lactose, starch, cellulose, hexites, synthetic polymers. Here, microcrystalline cellulose is particularly preferred. Here, microcrystalline cellulose is preferably contained in an amount of 95.0 mg to 105.0 mg per 1000 mg of a mesalazine high-dose tablet.

For example, decomposition aids are selected from the group comprising starch, cellulose, cellulose derivatives, synthetic polymers. Here, croscarmellose sodium is particularly preferred. Here, croscarmellose sodium is preferably contained in an amount of 57.0 mg to 63.0 mg per 1000 mg of a mesalazine high-dose tablet.

For example, flow control agents are selected from the group comprising starch, metallic soaps, anhydrous highly disperse silica. Here, anhydrous highly disperse silica is particularly preferred. Here, anhydrous highly disperse silica is preferably contained in an amount of 4.75 mg to 5.25 mg per 1000 mg of a mesalazine high-dose tablet.

For example, lubricants are selected from the group comprising metallic soaps, fatty alcohols, talcum, high-molecular polyethylene glycols. Here, calcium stearate is particularly preferred. Here, calcium stearate is preferably contained in an amount of 12.4 mg to 13.7 mg per 1000 mg of a mesalazine high-dose tablet.

Moreover, the at least one excipient does not contain any matrix-forming substances. As used herein, matrix-forming substances mean all substances that embed the active substance in a skeleton and so influence the release of the active substance. Examples of matrix-forming substances are cellulose derivatives, such as for example ethylcellulose, hydroxypropylmethylcellulose, waxes, polyvinyl acetate, polymers and copolymers of acrylates and methacrylates, such as for example Eudragit® of the RL, RS or NE types, without being restrictive. As the matrix-forming substances in the meaning of the present invention such additives are understood that are present in the tablet core and cause a delay of the release of the active ingredient.

The high-dose film coated tablet according to the present invention is characterized in that the mass of the high-dose film coated tablet is at most 40% higher than the mass of the active substance. That means that for example a tablet of a mass of active substance of 1000 mg has at most a total mass of 1400 mg.

In one embodiment the mass of the tablet core of the high-dose tablet is at most 40% higher, preferably at most 35% higher, and particularly preferred at most 30% and especially preferred at most 25% higher than the mass of the active substance.

In a further embodiment the proportion of the at least one excipient is at most 35% by weight and particularly preferred at most 20% by weight based on the total weight of the high-dose tablet.

Here, it is only a theoretic option to develop a 1000 mg high-dose tablet based on the recipe of the Salofalk® 500 mg enteric tablet by simply doubling the substances since this procedure would no longer result in deglutible molded articles of a mass of ca. 1.7 g. In this case, the mass of the tablet is 70% higher than the pure active ingredient proportion.

In contrast to that, the high-dose tablet according to the invention that has equivalent bio-pharmaceutical and therapeutic properties with Salofalk® 500 mg enteric tablets manages with a excipient proportion of only ca. 25%, so that the mass of the tablet is at most 35% higher than the pure active ingredient proportion. As outlined in example 1 the 1000 mg high-dose tablet according to the invention has only a mass of 1.3 g. Thus, while maintaining functionality these molded articles are significantly reduced in size and much more suited for an oral application than tablet recipes prepared by simply doubling. This is connected to an enhanced patient acceptance.

The high-dose tablet according to the invention consists of a tablet core of optimized dimensions in view of shape and size and in one embodiment at least one film coating. The tablet core is prepared by compressing a powder blend. It contains the active ingredient granule in a mixture with at least one excipient. Here, the total amount of active ingredient per tablet is processed in the granule.

In contrast to the at least one excipient the at least one film coating can contain matrix-forming substances. The at least one film coating can be applied in several layers. It is particularly preferred to apply 2, 3 or more layers. These layers can consist of both the same and different film-forming substances. Preferably, according to the invention there are used such film coatings that do not form a matrix, but dissolve in vivo. The at least one film coating is selected from the list of film-forming substances consisting of hypromellose, celluloseacetate phthalate; hydroxypropylmethylcellulose phthalate, hydroxypropylmethylcellulose acetate succinate, polyvinylacetate phthalate, shellac, anionic copolymers of methacrylic acid and their esters of the Eudragit® type, such as for example Eudragit® L, Eudragit® S, or mixtures thereof.

In a preferred embodiment the film coating consists of a primer coating as well as two layers that serve to ensure the retarded release of the active ingredient. For example, the primer coating consists of hypromellose and the layers that serve to ensure the retarded release of the active ingredient consist of Eudragit® L and Eudragit® S. As to the release of the active ingredient in vivo the primer coating is neutral. The primer coating neither alone nor in combination with the outer coating layers accelerates the release of the active ingredient.

In a particularly preferred embodiment the high-dose tablet according to the invention has a relatively thin "primer coating" of hypromellose (hydroxypropylmethylcellulose). One advantage of said primer coating is that the enteric coating attached thereto can be applied better and more evenly and that thereby also thinner layers of the enteric coating consisting of one or two layers can be applied. Finally, this results in the fact that less coating material is applied based on the active ingredient content and still the desired release profile can be achieved.

In a further preferred embodiment the film coating consists of two layers that serve to ensure the retarded release of the active ingredient. For example, the two layers consist of Eudragit® L or Eudragit® S or mixtures of Eudragit® S and L.

In a preferred embodiment the active ingredient granule is prepared by wet granulation of mesalazine with a binder solution consisting of water as the solvent and a water-soluble polymer, preferably povidone K25, as the binder. Here, the added amount of povidone K25 corresponds to 66.5 mg to 73.5 mg per tablet. Following wet screening and drying of the active ingredient granules excipients for improving the decomposition property, preferably croscarmellose sodium in an amount of 57.0 mg to 63.0 mg per tablet, dry binder, preferably microcrystalline cellulose in an amount of 95.0 mg to 105.0 mg per tablet, flow control agents, preferably anhydrous highly disperse silica in an amount of 4.75 mg to 5.25 mg per tablet, and lubricant, preferably calcium stearate in an amount of 12.4 mg to 13.7 mg per tablet are added.

The final mixture consisting of active ingredient granule and further excipients can be deformed very well. By compressing the mixed granule there result tablet cores that with a mass of 1248 mg per unit have an active ingredient proportion of 80%. Surprisingly, these tablet cores despite the high active ingredient proportion exhibit excellent mechanical properties as well as a rapid and complete disintegration as an important requirement for drug release after dissolution of the film coating. Strength of the compacts can be evaluated by determining the resistance to fracture and abrasion. Both properties are preferably determined in accordance with methods 2.9.7 and 2.9.8 of the European Pharmacopoeia. Resistance to fracture of the mesalazine high-dose tablets according to the invention is above 160 N, abrasion resistance or abrasion wear, respectively is less than 1%. Disintegration time of the tablet cores in 0.3 molar phosphate puffer pH 6.8, preferably determined according to method 2.9.1 of the European Pharmacopoeia, is less than 15 minutes.

Surprisingly, the tablet core of the application according to the invention manages with less excipients than known recipes of the tablet core such as e.g., those of Salofalk® 500 mg enteric tablets without changing the properties of the molded article. Here, the active ingredient granule of the 1000 mg high-dose tablets only consisting of mesalazine and povidone K25 results in the identical bio-pharmaceutical and therapeutic properties as the significantly more complex granule of Salofalk® 500 mg enteric tablets that for solubilizing the active ingredient additionally contain the excipients sodium carbonate and glycine. According to the invention these two substances can be cancelled in the preferred embodiment without replacement. Namely it has surprisingly been found in the present invention that for a complete pH controlled release and availability it can be refrained from the use of sodium carbonate and glycine. Refraining from sodium carbonate also enables that the active ingredient granule of the 1000 mg high-dose tablet according to the invention can be prepared purely aqueous and not by using an organic solvent such as ethanol. Efficacy of the present high-dose tablet in use was confirmed by comparative clinical study.

In addition to the improved granule recipe and product shape the optimized qualitative and quantitative composition of the film coating of the mesalazine 1000 mg high-dose tablet has to be mentioned as a further decisive and surprising feature of the invention. Thus, the process of film coating is significantly simplified and accelerated without impairing the desired releasing behavior of the active ingredient. This ensures that with a simplified dosage scheme as well as an enhanced patient acceptance the same therapeutic efficacy is achieved as with taking twice the number of Salofalk® 500 mg enteric tablets.

It is known that the successful treatment of the acute episode of ulcerative colitis as well as the prevention of recurrency with Salofalk® 500 mg enteric tablets require a defined release profile of mesalazine from the dosage form. Local availability of the active ingredient starts after the stomach passage with a further time delay of at least 15 minutes in the small intestine. That is, on the one hand the film coating has to ensure resistance to gastric juice of the form of administration and on the other hand may only completely be dissolved at least 15 minutes after stomach passage in the small intestine in order to ensure the start of the active ingredient release at the desired target site. With Salofalk® 500 mg enteric tablets such a release behavior is achieved by sequentially applying three layers of 90.5 mg of methacrylic acid methylmethacrylate copolymer (1:1) in total per tablet based on a surface of ca. 3.7 cm$^2$ (corresponding to 25 mg/cm$^2$ and a coat of 13%). This is an anionic polymer of methacrylic acid and methylmethacrylate of the trade name Eudragit® L. The ratio of the free carboxy groups to the ester groups is 1:1 and determines the solubility of the polymer from a pH value of 6.0. In association with the amount of film applied this ensures resistance to gastric juice as well as the start of the active ingredient release at the target site. Additionally, the tablet cores are isolated with a non-functional hypromellose layer before the methacrylic acid methylmethacrylate copolymer (1:1) is applied.

The "primer coating" that is preferably used according to the invention and preferably consists of an enteric coating material such as hydroxypropylmethylcellulose dissolves in the intestine independent of the pH value after the enteric outer coating has been dissolved. However, release of the active ingredient is not accelerated or otherwise modified by said primer coating.

The 1000 mg high-dose tablet according to the invention ensures the required release behavior of mesalazine in the small intestine by the fact that the tablets need to be coated with significantly less polymer material. In contrast to Salofalk® 500 mg enteric tablets the coating only includes 72.0 mg of a film-forming agent per tablet based on a surface of ca. 5.3 cm$^2$ (which corresponds to 14 mg/cm$^2$ and a coat of 6%). This marked reduction of the film amount is associated with an optimized qualitative composition of the coating material for the retarded release of active ingredient that only needs to be applied in two layers instead of three. Here, as the film-forming agent two copolymers of the Eudragit® type are used. In addition to Eudragit® L a mixture of Eudragit® L and Eudragit® S is used. Eudragit® S is the trade name for an anionic polymer of methacrylic acid and methylmethacrylate, wherein the ratio of the free carboxy groups to the ester groups is 1:2. Solubility of said copolymer is given at a pH value of 7.0 and above.

As outlined in example 1 the tablet cores isolated with hypromellose in the preferred embodiment at first are coated with a layer of methacrylic acid methylmethacrylate copolymer (1:1). Here, 47.2 mg of the polymer are applied to the surface of each tablet core (which corresponds to 9 mg/cm$^2$ and a coat of 4%). Subsequently, in a second layer a mixture consisting of 60% by weight of methacrylic acid methylmethacrylate copolymer (1:1) and 40% by weight of methacrylic acid methylmethacrylate copolymer (1:2) is added. The film resulting from said mixture coats each tablet surface with a further polymer material (which corresponds to 5 mg/cm$^2$ and a coat of only about 2%) consisting of Eudragit® L and Eudragit® S.

By the optimized qualitative and quantitative composition of the film coating of the mesalazine 1000 mg high-dose tablet the resistance to gastric juice as well as the desired release behavior in the upper small intestine are realized by a markedly less coat of polymer material. This results in a much simpler concept of coating the tablet cores. Comparative studies on active ingredient release in-vitro show identical resolution profiles between the high-dose tablet according to the invention as well as the Salofalk 500 mg enteric tablets in artificial intestinal juice with the required delay time of at least 15 minutes in vitro. Also resistance to gastric juice is ensured. Example 3 shows the results of the comparative active ingredient release tests.

Performing comparative active ingredient release tests, as shown in example 3, is an important means for selecting formulations since the results can be used to predict the bio-pharmaceutical and therapeutic properties. If two formulations to be compared behave identical in these tests conclusions to the actual in-viva situation in the patient are possible.

The in-vitro release apparatus used as standards, such as rotary basket and blade stirrer apparatus, are only partially suitable, since they cannot suitably simulate the relevant conditions of the gastro-intestinal passage. These are different passage and retention times, composition and volume of the gastro-intestinal fluid as well as hydrodynamic conditions. The more exact the gastro-intestinal segments are simulated in vitro, the better the predictions on the actual behavior of the dosage form in vivo.

The far better method to predict the product behavior under the condition after the intake by the patient is to simulate the gastro-intestinal passage as true as possible. Particularly suitable for that is the apparatus of the dipping cylinder (apparatus 3 according to chapter 2.9.3 of the European Pharmacopoeia). Said system allows characterization and comparison of dosage forms taking into account biologically relevant examination conditions. These are multiple media exchange, use of a smaller test volume as well as simulation of transport movements. Example 6 shows the results of the active ingredient release tests of the 1000 mg high-dose tablet according to the invention in comparison with Salofalk 500 mg enteric tablets using the apparatus of the dipping cylinder.

In a particularly preferred embodiment a high-dose tablet according to the invention with 1000 mg of mesalazine has a release profile of the active ingredient in the biodissolution test, as shown in example 6, that substantially corresponds to the release profile of two 500 mg tablets. That means that up to 120 min less than 10% of active ingredient are dissolved and that after 180 min 70% or preferably at least 80% more active ingredient are dissolved.

In a further preferred embodiment the high-dose tablets are oblong with parallel longitudinal sides and rounded narrow sides. The surfaces are biconvex curved and free from notches or breakage grooves. Here, the tablet height h is in the range of 6 to 8 mm, preferably in the range of 6.8 mm to 7.4 mm, particularly preferred 7.1 mm. The tablet length l is in the range of 19 to 22 mm, preferably in the range of 20 mm to 21 mm, particularly preferred in the range of 20.1 mm to 20.6 mm, such as for example 20.3 mm. The tablet width b is in the range of 8 to 10 mm, preferably in the range of 9 mm to 9.8 mm, particularly preferred in the range of 9.2 mm to 9.7 mm, such as for example 9.4 mm.

Radii of curvature (double curvature) of the convex top and bottom sides of the oblong tablet are 4.25 mm and 60.00 mm in the longitudinal direction and 4.25 mm and 8.00 mm in the transverse direction and allow an optimum coating of the tablets as well as enhanced swallowability of the coated tablets.

Example 2 describes the dimensions of the mesalazine 1000 mg high-dose tablets according to the invention. The tablet surface is ca, 5 cm$^2$. The chosen tablet size results in stable molded articles with optimum mechanical and geometric properties for application of even and thin film coatings in the drum coater. At the same time by the shape and dimensions swallowability and thus, acceptance of the tablets by the patients are enhanced to a great extent.

The described features of the invention result in the provision of a stable mesalazine 1000 mg high-dose tablet. Primary package of the tablets preferably is in blisters consisting of PVC or PVC plastic forming foils coated with PVDC and hard aluminum covering foil. Qualitative and quantitative composition as well as the manufacturing method chosen and choice of the primary packaging means ensure that the tablets do not show changes at storage under climatic zone II conditions over a period of at least 36 months. Also under the conditions of loading tests the tablets are stable. The results of durability tests are outlined in example 4.

Moreover, the present invention relates to the use of mesalazine-containing high-dose tablets as described above in the treatment of chronic inflammatory bowel diseases. In one embodiment the mesalazine 1000 mg high-dose tablet according to the invention such as Salofalk® 500 mg enteric tablets is used in the treatment of an acute episode of ulcerative colitis as well as prevention of recurrency.

In a clinical study with the aim to show that the high-dose tablet according to the invention can be compared with the 500 mg tablets described in the prior art both formulations were tested over a period of 8 weeks. A total of 306 patients suffering from an active ulcerative colitis were treated in a double-blind (double-dummy) clinical study in several European countries either with the 1000 mg mesalazine tablet according to the invention (intake three times a day) or 2×500 mg of mesalazine tablets (also intake three times a day). Patients who achieved a clinical remission after 8 weeks of treatment (visit 4 of the patients) were evaluated as successfully treated. Clinical remission was very stringent defined as a disease activity index≤4 (CAI, Colitis Activity Index) with a daily defecation frequency in said index of 0 (defined as <18 defecations per week) and a sub-score for rectal bleeding of 0 too (defined as 0-1 bloody defecations in said sub-score). Example 5 shows the results of the study in the various statistical evaluation populations. The clinical study could be terminated already after the intermediate analysis due to the comparable efficacy. In the treatment group having taken the high-dose tablet according to the invention (M1000) 46.6% of the patients achieved the primary proof of efficacy compared to 38.6% of the patients in the treatment group with 2×500 mg mesalazine tablets (M2×500) daily (example 5).

Therapeutic efficacy, safety and tolerance of mesalazine are equally ensured by both formulations. In view of these criteria there is no difference between the Salofalk® 500 mg enteric tablet and the mesalazine 1000 mg high-dose tablet according to the invention.

However, the patients clearly prefer the medicamentous treatment with the mesalazine 1000 mg high-dose tablet. A great majority of the patients (47.7%) clearly speak out in favor of the intake of only one tablet. Only 10.5% of the patients participating in the study preferred the intake of two smaller mesalazine tablets. The result is robust since all the patients in the double-blind clinical study have taken both forms of administration, either as a placebo or as a verum during the study. This surprisingly clear vote can be attributed to the chosen shape and size of the high-dose tablet and thus, to a much more simplified and patient-friendly dosage and administration scheme, whereby the regular intake of medicaments is facilitated and the acceptance by the patients is enhanced. Accordingly, with the mesalazine 1000 mg high-dose tablet according to the invention compliance can be enhanced, so that a proportionally higher success of the mesalazine therapy can be achieved compared to the tested established forms of administration. Thus, therapy and patient related factors as causes for non-compliance can significantly be reduced with the high-dose tablet according to the invention.

Preferred embodiments of the present invention are made evident by the following examples.

EXAMPLE 1: QUALITATIVE AND QUANTITATIVE COMPOSITION OF THE PREFERRED EMBODIMENTS OF A MESALAZINE ENTERIC 1000 MG HIGH-DOSE TABLET

TABLE 1

| Substance | Mass per Tablet |
| --- | --- |
| Mesalazine | 1000.00 mg |
| Povidone K25 | 70.00 mg |
| Microcrystalline Cellulose | 100.00 mg |
| Anhydrous highly disperse silica | 5.00 mg |
| Croscarmellose sodium | 60.00 mg |
| Calcium stearate | 13.00 mg |
| Hypromellose | 6.50 mg |
| Macrogol 6000 | 7.60 mg |

TABLE 1-continued

| Substance | Mass per Tablet |
|---|---|
| Methacrylic acid methylmethacrylate copolymer 1:1 | 57.10 mg |
| Methaerylic acid methylmethacrylate copolymer 1:2 | 14.90 mg |
| Talcum | 12.05 mg |
| Titanium dioxide | 0.60 mg |
| Iron oxide, yellow | 0.75 mg |
| Mass of coated tablet | 1347.50 mg |

The composition of a preferred 1000 mg high-dose tablet is given in table 1.

The above substances of the tablet core: mesalazine, Povidone K25, microcrystalline cellulose, anhydrous highly disperse silica, croscarrnellose sodium and calcium stearate all add up to 1248 mg. This represents 80.1% by weight of the ready-made tablet. Thus, the proportion of the coatings is less than 20.0% by weight of the finished tablet.

EXAMPLE 2: TABLET SHAPE. TABLET SIZE, TABLET GEOMETRY AS WELL AS TABLET DIMENSIONS OF MESALAZINE ENTERIC 1000 MG HIGH-DOSE TABLETS

Tablet Geometry

| shape, appearance | oblong, rod-shaped |
|---|---|
| sides | parallel to slightly rounded longitudinal and rounded narrow sides |
| surface | biconvex curved surfaces, free from notches or breakage grooves |

Tablet Size and Dimensions (without Film Coating)

| Tablet height | 7.1 mm (6.8 mm to 7.4 mm) |
|---|---|
| Tablet length | 20.3 mm (20.1 mm to 20.6 mm) |
| Tablet width | 9.4 mm (9.2 mm to 9.7 mm) |
| Height of edge | 3.2 mm (2.9 mm to 3.5 mm) |
| Height of spherical cap | 1.95 mm |
| Circumference | 5.1 cm |
| Surface of circumferential or edge, resp. | 1.64 cm$^2$ |
| Projected area | 1.84 cm$^2$ |
| Surface | 5.32 cm$^2$ (5.16 cm$^2$ to 5.47 cm$^2$) |

Figure 2:
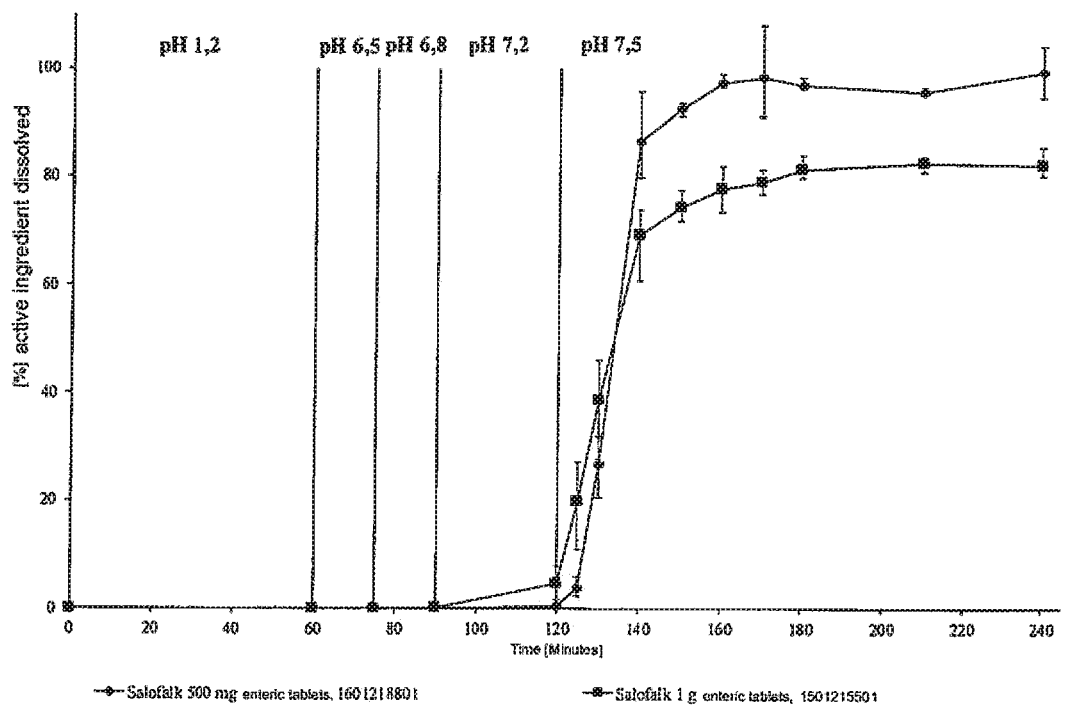

Tablet Curvature (Radii of Curvature of the Spherical Cap)
  curvature radii, longitudinal
    Radius 1: 4.25 mm
    Radius 2: 60.00 mm
  curvature radii, transverse
    Radius 1: 4.25 mm
    Radius 2: 8.00 mm
  FIG. 1 is a graph showing percent mesalazine release profiles of mesalazine enteric 1000 mg high-dose tablets and 500 mg enteric tablets.
  FIG. 2 is a graph showing percent active ingredient dissolved profiles of mesalazine enteric 1000 mg high-dose tablets and 500 mg enteric tablets.

EXAMPLE 3: PROOF OF EQUIVALENT ACTIVE INGREDIENT RELEASE PROFILES OF MESALAZINE ENTERIC 1000 MG HIGH-DOSE TABLETS AND SALOFALK® 500 MG ENTERIC TABLETS

A high-dose tablet (1000 mg) according to the invention shows an equivalent resolution profile of mesalazine as two Salofalk® 500 mg enteric tablets. Here, in the preferred embodiment comparable studies on active ingredient release in vitro were performed with two different batches of mesalazine enteric 1000 mg high-dose tablets and included the test over two hours in artificial gastric juice with a pH value of 1 (0.1 M HCl) as well as the subsequent test over 60 minutes in artificial intestinal juice with a pH value of 6.8 (0.3 M phosphate buffer). After exposition in artificial gastric juice the film coated tablets of the reference preparation, i.e. Salofalk® 500 mg enteric tablets, and the film coated tablets of the invention, i.e. mesalazine enteric 1000 mg high-dose tablets, showed identical resolution profiles of mesalazine in artificial intestinal juice. After the required delay time of at least 15 minutes the release profiles run approximately coincident and after 60 minutes the complete dissolution of mesalazine has been achieved. The amounts of mesalazine released after the individual test times in artificial intestinal juice differ between the reference preparation and the high-dose tablet according to the invention by less than 10%. According to the guidelines of the European Medicines Agency (PMA) on bioequivalence studies (CPMP/EWP/QWP/1401/98 Rev. 1/Corr.) a similarity factor (f2) greater than 50 can be calculated from the results of the comparing active ingredient release tests. Thus, the profiles are considered to be identical. The following explanations summarize the tests in detail.
  a) Test Pattern
  mesalazine enteric 1000 mg high-dose tablet, batches G0605B001, G0605B002
  Salofalk® 500 mg enteric tablets, batch 1204966001
  b) Parameters of the Active Ingredient Release Test
  release apparatus: blade stirrer apparatus (apparatus 2 according to chapter 2.9.3 of the European Pharmacopoeia)
  Test media
    artificial gastric juice: 0.1 M HCl, volume 500 ml, 120 minutes
    artificial intestinal juice: 0.3 M phosphate buffer pH 6.8, volume 1000 ml, 60 minutes
  temperature 37.0° C.±0.5° C.
  stirring speed: 100 rpm
  number of samples per test time and batch: N=12
  test times: 0, 5, 10, 15, 20, 25, 30, 35, 45, 60 minutes
  c) Content Determining Method for Mesalazine
  The content of the amount of mesalazine released in the test medium was spectro-photometrically determined at a wave length of 370 nm.
  d) Results
  FIG. 1 shows the release profiles of the three tested batches.
  The calculation of the similarity factor (f2) at the final test time yielded the following results:
  mesalazine enteric 1000 mg high-dose tablet, batch G0605B001, and Salofalk 500 mg enteric tablet, batch 1204966001: f2=66
  mesalazine enteric 1000 mg high-dose tablet, batch G0605B002, and Salofalk 500 mg enteric tablet, batch 1204966001: f2=53

EXAMPLE 4: RESULTS OF DURABILITY STUDIES ON MESALAZINE ENTERIC 1000 MG HIGH-DOSE TABLETS

Two batches of mesalazine enteric 1000 mg high-dose tablets were prepared in the preferred embodiment, packed into blisters consisting of PVDC/PVC aluminum foils and stored at 25° C./60% relative humidity and 40° C./75% relative humidity for durability studies. After preparation and in regular intervals during storage both the content and purity of the film coated tablets as well as release of active ingredient were determined. Here, determination of content and purity was performed with a validated HPLC/UV method, while the determination of the active ingredient release from the film coated tablets was spectro-photometrically performed at a wave length of 370 nm. The high-dose tablet according to the invention neither under long-term conditions (36 months at 25° C./60% relative humidity) nor under accelerated conditions (6 months at 40° C./75% relative humidity) shows changes in the tested properties. The two following tables 2 and 3 summarize the results of the durability studies of the two batches

TABLE 2

Mesalazine enteric 1000 mg high-dose tablet, batch G0605B001
Primary packaging means: PVC/PVDC aluminum blister[1]

| Test parameters | Storage time (months) at 25° C./60% relative humidity | | | | | | |
|---|---|---|---|---|---|---|---|
| | 0 | 6 | 9 | 12 | 18 | 24 | 36 |
| Mesalazine content (%) | 97.0 | 96.6 | 98.5 | 98.0 | 100.0 | 98.9 | 97.5 |
| Sum of disintegration products (%) | 0.07 | 0.05 | 0.06 | 0.11 | 0.21 | <0.05 | 0.15 |
| Active ingredient release at 37° C. (%) | | | | | | | |
| in 0.1M HCl (120 minutes) | resistant | resistant | resistant | resistant | resistant | resistant | resistant |
| in buffer pH 6.8 (15 minutes) | 0.8 | 0.1 | 0.1 | 0.4 | 0.3 | 0.5 | 0.5 |
| in buffer pH 6.8 (60 minutes) | 93.2 | 94.4 | 84.4 | 95.0 | 91.3 | 92.5 | 92.6 |

| | Storage time (months) at 40° C./75% relative humidity | | |
|---|---|---|---|
| | 0 | 3 | 6 |
| Mesalazine content (%) | 97.0 | 97.7 | 97,0 |
| Sum of disintegration product (%) | 0.07 | 0.07 | 0.09 |
| Active ingredient release at 37° C. (%) | | | |
| in 0.1M HCl (120 minutes) | resistant | resistant | resistant |
| in buffer pH 6.8 (15 minutes) | 0.8 | 0.5 | 0.1 |
| in buffer pH 6.8 (60 minutes) | 93.2 | 93.0 | 90.5 |

[1]PVC/PVDC foil (250 μm, 60 g/m², orange), aluminum foil (20 μm)

TABLE 3

Mesalazine enteric 1000 mg high-dose tablet, batch G0605B002
Primary packaging means: PVC/PVDC aluminum blister[1]

| Test parameters | Storage time (months) at 25° C./60% relative humidity | | | | | | |
|---|---|---|---|---|---|---|---|
| | 0 | 6 | 9 | 12 | 18 | 24 | 36 |
| Mesalazine content (%) | 98.5 | 101.6 | 97.0 | 100.6 | 99.6 | 100.4 | 98.2 |
| Sum of disintegration products (%) | 0.07 | 0.13 | 0.21 | 0.05 | 0.22 | 0.06 | 0.15 |
| Active ingredient release at 37° C. (%) | | | | | | | |
| in 0.1M HCl (120 minutes) | resistant | resistant | resistant | resistant | resistant | resistant | resistant |
| in buffer pH 6.8 (15 minutes) | 3.2 | 2.9 | 2.9 | 4.1 | 3.8 | 2.3 | 3.7 |
| in buffer pH 6.8 (60 minutes) | 92.3 | 91.4 | 95.2 | 96.9 | 96.3 | 95.4 | 92.5 |

| | Storage time (months) at 40° C./75% relative humidity | | |
|---|---|---|---|
| | 0 | 3 | 6 |
| Mesalazine (%) | 98.5 | 96.2 | 102.4 |
| Sum of disintegration products (%) | 0.07 | 0.06 | 0.07 |
| Active ingredient release at 37° C. (%) | | | |
| in 0.1M HCl (120 minutes) | resistant | resistant | resistant |
| in buffer pH 6.8 (15 minutes) | 3.2 | 2.6 | 1.3 |
| in buffer pH 6.8 (60 minutes) | 92.3 | 99.5 | 93.7 |

[1]PVC/PVDC foil (250 μm, 60 g/m², orange), aluminum foil (20 μm)

EXAMPLE 5: CLINICAL DATA

The results of the clinical study are summarized in table 4.

| Analysis approach | Number (%) of patients in clinical remission at V4-LOCF | | | | | | Diff[a] | 95%-RCI[b] | Sign. level[c] | P value[d] |
|---|---|---|---|---|---|---|---|---|---|---|
| | M1000 | | | M2x500 | | | | | | |
| | N | n | % | N | n | % | | | | |
| PP Interim I[e] | 103 | 48 | 46.6 | 114 | 44 | 38.6 | 8.0% | [−9.6%, 25.2%] | 0.0043 | 0.0003 |
| FAS Interim I | 115 | 53 | 46.1 | 123 | 46 | 37.4 | 8.7% | [−8.1%, 25.0%] | 0.0043 | <0.0001 |
| PP Final[f] | 134 | 64 | 47.8 | 144 | 61 | 42.4 | 5.4% | [−10.2%, 20.8%] | 0.0043 | 0.0003 |
| FAS Final[f] | 151 | 68 | 45.0 | 155 | 65 | 41.9 | 3.1% | [−11.7%, 17.8%] | 0.0043 | 0.0006 |

[a]difference between proportions ($\pi$M100 − $\pi$M2x500)
[b]repeated 95% confidence interval (RCI)
[c]single-sided local significance level
[d]test of $H_0$ ($\pi$M1000 − $\pi$M2x500 ≤ −0.15) by inverse normal test statistics
[e]primary analysis
[f]PP/FAS analysis approaches taking into account 68 overrunning patients taken up into the study during the interim analysis I In table 4 PP describes the Per Protocol analysis and FAS the analysis in the "Full Analysis Set", wherein the patients of the PP population have carried out the study according to the protocol and in the FAS population all 306 patients were evaluated who were included in this study.

EXAMPLE 6: "BIO-DISSOLUTION TEST" OF THE HIGH-DOSE TABLET ACCORDING TO THE INVENTION

To objectify and put into perspective the deviations in resolution that necessarily occur in the individual patients a so-called "Biodissolution" test was performed in vitro.

To proof the equivalent active ingredient release profiles of mesalazine enteric 1000 mg high-dose tablet and Salofalk 500 mg enteric tablets under biologically relevant test conditions the following test was performed:

Using the apparatus of the dipping cylinder (apparatus 3 according to chapter 2.9.3 of the European Pharmacopoeia) allows comparing the delayed release of mesalazine from the high-dose tablet according to the invention as well as from Salofalk 500 mg enteric tablets under biologically relevant conditions. Here, one dose of the tablets each is in a vial that is closed upwards and downwards with a wire mesh to hold the dosage form. Said glass cylinder is moved up and down in a dissolving vessel of a volume of ca. 325 ml. In contrast to standard apparatus for determining the active ingredient release with this system a number of test media can be studied. The glass cylinder moves in a vertical moving direction ca, 10 cm in the dissolving vessel containing 200 ml of the test medium. Here, the speed of movement is 10 dipping movements per minute (dips per minute, dpm). The advantages of the system are that by a multiple media exchange in the dissolving vessel the tablets contact different test liquids and thus, gastro intestinal passage can be simulated.

For the tests 1000 mg high-dose tablets according to the invention and Salofalk 500 mg enteric tablets of commercial production batches were used. For comparison of both tablet shapes in total five test media were used that especially simulate the pH conditions of the individual segments of the gastro intestinal tract in fasting state. The retention times in the individual media in combination with the agitation movements correspond to the conditions the dosage form is also subjected to in vivo. The test results impressively show that the active ingredient release of mesalazine from the high-dose tablet according to the invention and from Salofalk 500 mg enteric tablets equally only takes place under the conditions of the distal ileum. Here, the active ingredient is completely released from the tablets and is available for local action. That is, the active ingredient is transported to the desired target site by the formulation. The following explanations summarize the tests in detail:

a) Test Pattern mesalazine enteric 1000 mg high-dose tablet, batch 1501215501

Salofalk 500 mg enteric tablets, batch 1601218801 b) Parameter of the Active Ingredient Release Test release apparatus: apparatus of dipping cylinder (apparatus 3 according to chapter 2.9.3 of the European Pharmacopoeia)

mesh size: 840 μm volume of each dissolution vessel: 200 ml temperature: 37.0±0.5° C.

dipping movements: 10 dipping movements per minute (dips per minute, dpm)

number of samples per test time and batch: N=6 test media and removal and test times, respectively:

| Segment of the gastrointestinal tract | pH value | Test medium | Removal and test times (minutes) |
|---|---|---|---|
| stomach | 1.2 | 0.1M HCl | 60 |
| proximal jejunum | 6.5 | phosphate buffer (Ph. Eur. 5.17.1) | 15 |
| distal jejunum | 6.8 | simulated intestinal fluid without pepsins ($SIF_{sp}$) (Ph. Eur. 5.17.1) | 15 |
| proximal ileum | 7.2 | phosphate buffer (Ph. Eur. 5.17.1) | 30 |
| distal ileum | 7.5 | simulated intestinal fluid without pepsins ($SIF_{sp}$) (Ph. Eur. 5.17.1)[1] | 5, 10, 20, 30, 40, 50, 60, 90, 120 |
| large intestine | | not tested | |

[1]calculated osmolarity ~0.5 osmol/l c) Determination of Content for Mesalazine Determination of the content of the amount of mesalazine released in the test medium was performed by high-performance liquid chromatography with UV/VIS detection (HPLC/UV). Detection wave length was 220 nm.

d) Results

FIG. 2 shows the release profiles of both tested batches.

The invention claimed is:

1. An oral enteric high-dose tablet comprising as an active substance 1000 mg of mesalazine or a pharmaceutically acceptable salt thereof and at least one excipient not containing matrix-forming substances, wherein the mass of the oral enteric high-dose tablet is at most 35% higher than the mass of the active substance, wherein the oral enteric high-dose tablet has a resistance to fracture of above 160 N, wherein a release profile in the biodissolution test of mesalazine substantially corresponds to a release profile of two tablets each containing half the amount of mesalazine of the oral enteric high-dose tablet, and wherein the oral enteric high-dose tablet comprises a tablet core, a primer coating on the tablet core wherein the primer coating does not accelerate or otherwise modify the release of the active ingredient, a first enteric coating layer comprising a methacrylic acid methylmethacrylate copolymer having a ratio of free carboxyl groups to ester groups of 1:1 on the primer coating, and a second enteric coating layer comprising a methacrylic acid methylmethacrylate copolymer having a ratio of free carboxyl groups to ester groups of 1:2, or a mixture of a methacrylic acid methylmethacrylate copolymer having a ratio of free carboxyl groups to ester groups of 1:1 and a methacrylic acid methylmethacrylate copolymer having a ratio of free carboxyl groups to ester groups of 1:2, on the first enteric coating layer, the oral enteric high-dose tablet having a release rate of active ingredient in a buffer with a pH of 6.8 of at least 90% within 60 minutes and wherein the first enteric coating layer and the second enteric coating layer makes up less than 10% by weight based on the total weight of the oral enteric high-dose tablet.

2. The oral enteric high-dose tablet according to claim 1, wherein the proportion of the at least one excipient makes up at most 30% by weight based on the total weight of the oral enteric high-dose tablet.

3. The oral enteric high-dose tablet according to claim 1, characterized in that the oral enteric high-dose tablet contains 50 to 100 mg of povidone.

4. The oral enteric high-dose tablet according to claim 1, wherein the oral enteric high-dose tablet has an oblong shape with parallel longitudinal sides and rounded narrow sides and the surfaces are biconvex curved and free from notches or breakage grooves.

5. The oral enteric high-dose tablet according to claim 1 utilized in the treatment of chronic inflammatory bowel diseases.

6. The oral enteric high-dose tablet according to claim 5 utilized in the treatment of ulcerative colitis.

7. The oral enteric high-dose tablet according to claim 6 utilized in the treatment of ulcerative colitis in the remission phase.

8. The oral enteric high-dose tablet according to claim 5 utilized for treatment of chronic inflammatory bowel diseases, wherein three oral enteric high-dose tablets are administered a day.

9. The oral enteric high-dose tablet according to claim 8, wherein one oral enteric high-dose tablet each is administered in the morning, noon and evening.

10. The oral enteric high-dose tablet according to claim 1, wherein the oral enteric high-dose tablet comprises at least one excipient consisting of polyvinyl pyrrolidone.

11. The oral enteric high-dose tablet according to claim 1, wherein said at least one excipient does not contain matrix-forming substances that embed the mesalazine active substance in a skeleton to delay the release of the mesalazine active substance.

12. The oral enteric high-dose tablet according to claim 1, wherein the oral enteric high-dose tablet completely dissolves in artificial intestinal juice comprising 0.3M phosphate buffer having pH 6.8 and a temperature of 37.0° C.±0.5° C. within 60 minutes.

13. The oral enteric high-dose tablet according to claim 11, wherein the oral enteric high-dose tablet completely dissolves in artificial intestinal juice comprising 0.3M phosphate buffer having pH 6.8 and a temperature of 37.0° C.±0.5° C. within 60 minutes.

14. The oral enteric high-dose tablet according to claim 12, wherein no active substance is dissolved in artificial gastric juice having a pH of 1 within 60 minutes.

\* \* \* \* \*